United States Patent
Allen et al.

(10) Patent No.: US 11,096,798 B2
(45) Date of Patent: Aug. 24, 2021

(54) ACETABULAR CUP ASSEMBLY FOR MULTIPLE BEARING MATERIALS

(71) Applicant: Smith & Nephew, Inc., Memphis, TN (US)

(72) Inventors: Charles Wayne Allen, Southaven, MS (US); Jason A. Capriotti, Senatobia, MS (US); Michael A. Croxton, The Woodlands, TX (US); Roger William Frank Ashton, Warwick (GB); Justin M. Waugh, Memphis, TN (US); Jeffrey J. Shea, Memphis, TN (US); Sureshkumar Srinivasan, Coimbatore (IN); William L. Waltersdorff, Hernando, MS (US); Terry W. McLean, Eads, TN (US)

(73) Assignee: Smith & Nephew, Inc., Memphis, TN (US)

( * ) Notice: Subject to any disclaimer, the term of this patent is extended or adjusted under 35 U.S.C. 154(b) by 21 days.

(21) Appl. No.: 16/460,753

(22) Filed: Jul. 2, 2019

(65) Prior Publication Data
US 2019/0321196 A1 Oct. 24, 2019

Related U.S. Application Data

(60) Division of application No. 15/288,568, filed on Oct. 7, 2016, now Pat. No. 10,383,745, which is a
(Continued)

(51) Int. Cl.
*A61F 2/46* (2006.01)
*A61F 2/30* (2006.01)
(Continued)

(52) U.S. Cl.
CPC ........ *A61F 2/4609* (2013.01); *A61F 2/30767* (2013.01); *A61F 2/32* (2013.01);
(Continued)

(58) Field of Classification Search
CPC .................................... A61F 2/34; A16F 2/32
(Continued)

(56) References Cited

U.S. PATENT DOCUMENTS

| 5,310,408 A | 5/1994 | Schryver et al. |
| 5,725,591 A | 3/1998 | DeCarlo, Jr. et al. |
| 2007/0106392 A1 | 5/2007 | Servidio et al. |

FOREIGN PATENT DOCUMENTS

| CN | 2426346 Y | 4/2001 |
| CN | 1294507 A | 5/2001 |

(Continued)

OTHER PUBLICATIONS

Chinese Search Report; State Intellectual Property Office of People's Republic of China; Chinese Patent Application No. 201310139807.9; dated Nov. 21, 2014; 5 pages.
(Continued)

*Primary Examiner* — Yashita Sharma
(74) *Attorney, Agent, or Firm* — Kacvinsky Daisak Bluni PLLC

(57) ABSTRACT

A modular acetabular cup assembly for use with multiple bearing liners is disclosed. The acetabular cup assembly includes a shell having a tapered inner wall and two circumferential grooves. The shell may be used with polyethylene, ceramic, metal, and other types of liners.

16 Claims, 14 Drawing Sheets

Related U.S. Application Data continuation of application No. 14/171,828, filed on Feb. 4, 2014, now Pat. No. 9,463,094, which is a continuation of application No. 12/293,705, filed as application No. PCT/US2006/060044 on Oct. 18, 2006, now Pat. No. 8,679,187.

(60) Provisional application No. 60/783,937, filed on Mar. 20, 2006.

(51) Int. Cl.
| | | |
|---|---|---|
| *A61F 2/32* | (2006.01) | |
| *A61F 2/34* | (2006.01) | |
| *A61B 17/68* | (2006.01) | |
| *A61B 17/86* | (2006.01) | |
| *A61F 2/36* | (2006.01) | |

(52) U.S. Cl.
CPC .............. *A61F 2/34* (2013.01); *A61F 2/4637* (2013.01); *A61F 2/4684* (2013.01); *A61B 17/68* (2013.01); *A61B 17/86* (2013.01); *A61F 2/30744* (2013.01); *A61F 2002/305* (2013.01); *A61F 2002/3052* (2013.01); *A61F 2002/3054* (2013.01); *A61F 2002/30092* (2013.01); *A61F 2002/3093* (2013.01); *A61F 2002/30321* (2013.01); *A61F 2002/30331* (2013.01); *A61F 2002/30332* (2013.01); *A61F 2002/30367* (2013.01); *A61F 2002/30378* (2013.01); *A61F 2002/30403* (2013.01); *A61F 2002/30474* (2013.01); *A61F 2002/30487* (2013.01); *A61F 2002/30495* (2013.01); *A61F 2002/30578* (2013.01); *A61F 2002/30593* (2013.01); *A61F 2002/30604* (2013.01); *A61F 2002/30607* (2013.01); *A61F 2002/30616* (2013.01); *A61F 2002/30787* (2013.01); *A61F 2002/30822* (2013.01); *A61F 2002/30827* (2013.01); *A61F 2002/30906* (2013.01); *A61F 2002/30925* (2013.01); *A61F 2002/30968* (2013.01); *A61F 2002/3216* (2013.01); *A61F 2002/3241* (2013.01); *A61F 2002/3401* (2013.01); *A61F 2002/3403* (2013.01); *A61F 2002/3611* (2013.01); *A61F 2002/4629* (2013.01); *A61F 2002/4632* (2013.01); *A61F 2002/4641* (2013.01); *A61F 2002/4666* (2013.01); *A61F 2002/4681* (2013.01); *A61F 2002/4688* (2013.01); *A61F 2210/0014* (2013.01); *A61F 2220/0025* (2013.01); *A61F 2220/0033* (2013.01); *A61F 2250/0025* (2013.01); *A61F 2250/0062* (2013.01); *A61F 2310/00017* (2013.01); *A61F 2310/00023* (2013.01); *A61F 2310/00029* (2013.01); *A61F 2310/00167* (2013.01); *A61F 2310/00179* (2013.01); *A61F 2310/00203* (2013.01); *A61F 2310/00239* (2013.01); *A61F 2310/00395* (2013.01)

(58) Field of Classification Search
USPC .......................................... 623/22.21–22.32
See application file for complete search history.

(56) References Cited

FOREIGN PATENT DOCUMENTS

| | | |
|---|---|---|
| CN | 1416330 A | 5/2003 |
| EP | 0245527 A1 | 11/1987 |
| EP | 1308141 A1 | 5/2003 |
| GB | 2159416 A | 12/1985 |

OTHER PUBLICATIONS

Chinese First Office Action; State Intellectual Property Office of People's Republic of China; Chinese Patent Application No. 201310139807.9; dated Dec. 1, 2014; 17 pages.

Chinese Second Office Action; State Intellectual Property Office of People's Republic of China; Chinese Patent Application No. 201310139807.9; dated Sep. 6, 2015; 8 pages.

International Preliminary Report on Patentability, The International Bureau of WIPO, International Application No. PCT/US2006/060044; dated Sep. 23, 2008; 1 page.

Written Opinion of the International Searching Authority; European Patent Office, International Application No. PCT/US2006/060044; dated Sep. 23, 2008; 5 pages.

ACETABULAR CUP ASSEMBLY FOR MULTIPLE BEARING MATERIALS

CROSS-REFERENCE TO RELATED APPLICATION

This application is a divisional of pending U.S. application Ser. No. 15/288,568, filed Oct. 7, 2016, which application is a continuation of U.S. application Ser. No. 14/171,828, filed Feb. 4, 2014 and now issued as U.S. Pat. No. 9,463,094, which is a continuation of U.S. application Ser. No. 12/293,705, filed Sep. 29, 2010 and now issued as U.S. Pat. No. 8,679,187, which is a U.S. National Phase filing of International Application No. PCT/US2006/060044, filed Oct. 18, 2006, which claims the benefit of U.S. Provisional Application No. 60/783,937, filed Mar. 20, 2006. The disclosure of each of these applications is hereby incorporated by reference in its entirety.

BACKGROUND OF THE INVENTION

Field of the Invention

The present invention relates to acetabular cups and, more particularly, to acetabular cup assemblies for use with multiple bearings.

Related Art

In hip arthroplasty, various bearing materials are available for the acetabular cup portion of an implant. The selection of the bearing material is typically determined by the surgeon prior to performance of the procedure. At times, however, final selection of the bearing material is not completed until the implant site is prepared and conditions at the site are evaluated. Thus, it is sometimes advantageous to utilize an acetabular shell that accepts multiple bearing liners so that the surgeon can revise the initial assessment if required.

Acetabular shells that accept multiple bearings have been used in Europe since the early 1980s. Typically, the outer shell featured a tapered inside geometry in which a tapered hard or soft bearing could be inserted. In these cases, soft bearing thickness, lock integrity and wear performance were compromised in an effort to accommodate both bearings.

More recently, Stryker Corp. of Kalamazoo, Mich., U.S.A., has developed an acetabular cup that accepts a fully metal-encapsulated ceramic insert, which is held via a taper lock connection. The shell also accepts a polyethylene insert that is locked via one circumferential bead located mid-point along the inner taper and is rotationally stabilized by four conforming features between the shell and the liner.

An acetabular cup assembly for use with multiple bearings is desirable from a manufacturing standpoint because it is only necessary to produce one shell for use in many applications. This increases the volume of shells produced, which decreases overall production costs. Further, production of a single shell reduces distribution costs.

An acetabular cup assembly for use with multiple bearings is desirable from a revision standpoint because it gives the surgeon greater flexibility and reduces the overall time of the operation. First, the assembly gives the surgeon greater flexibility because the surgeon can easily make adjustments to the hip prosthesis. For example, if the original prosthesis had a polyethylene liner, the surgeon can easily substitute a ceramic or metal liner without changing the shell. Second, the assembly reduces the overall operation time because it is not necessary to remove the shell. Typically, the installed shell is surrounded by ingrown bone, which is very difficult and time consuming to remove. Further, removal of the installed shell may result in significant bone loss. By eliminating the step of removing the shell, the surgeon can complete the revision in less time with less effort and the result is less traumatic to the patient.

Micromotion between a polyethylene liner and an acetabular shell is undesirable as the motion creates polyethylene debris, which eventually causes bone osteolysis. Prior polyethylene bearing lock mechanism were designed to exhibit minimal micromotion between the liner and the shell. However, these mechanisms also required an excessive interoperative insertion force for insertion of the liner. A high insertion force is undesirable as it requires greater effort on behalf of the surgeon to install the liner.

Traditionally, ceramic liner manufacturers have advised against reinsertion of ceramic liners due to the stress sensitive nature of the material. The material may fracture at break if stressed inappropriately. However, for various reasons, it may be desirable to remove and reinstall a liner. As an example, a surgeon may want to remove the ceramic liner during installation change the shell position, and reinstall the liner. As ceramic manufactures presently advise against this, a surgeon takes on great risk when making these types of adjustments during ceramic liner installation.

There remains a need in the art for an acetabular cup assembly for use with multiple bearings.

SUMMARY OF THE INVENTION

The invention is briefly, an acetabular cup assembly. The assembly includes a shell and a liner. The shell has an inner surface and an outer surface. The inner surface has a first groove, a second groove, and a tapered inner wall. The liner is adapted to fit within the inner surface of the shell. The liner is selected from the group consisting of a polymer liner, a ceramic liner, and a metal liner, and the polymer liner has an inner portion and an outer portion, the outer portion includes a first bump and a second bump, the ceramic liner includes a band, and the metal liner includes a tapered outer portion.

In one embodiment of the invention, the polymer liner is selected from the group consisting of cross-linked polyethylene and conventional polyethylene.

In another embodiment of the invention, the liner includes anti-rotation tabs and the shell includes at least one scallop. The scallops are dimensioned to receive the anti-rotation tabs.

In yet another embodiment of the invention, the shell includes an insertion tool hole.

The insertion tool hole may be used in conjunction with a tool to install the shell.

In still another embodiment of the invention, the inner surface of the shell is highly polished. The inner surface may have a surface roughness of about one to about sixteen microinches, and rather about one to about eight microinches. The highly polished surface reduces polymer liner debris if micromotion happens to occur between the shell and the liner.

In another embodiment of the invention, the shell is made from a material selected from the group consisting of titanium, cobalt chromium, and stainless steel.

In yet another embodiment of the invention, the shell further comprises at least one fixation hole. The fixation hole is adapted to receive one or more fixation devices to attach the shell to bone.

In still another embodiment of the invention, the shell further comprises a porous coating on the outer surface. The porous touting allows for bone in growth.

In another embodiment of the invention, the band has a taper. The band may be tapered from about two degrees to about thirty-six degrees, and rather the band has a taper of about eighteen degrees.

In yet another embodiment of the invention, the tapered inner wall, the band or the tapered outer portion includes a surface enhancement. The surface enhancement may be selected from the group consisting of an acme-type stair-step, a reverse stair-step, or a predetermined surface roughness. The surface enhancement augments the locking of the liner.

In still another embodiment of the invention, the acetabular cup assembly may have a constrained bearing liner. The liner may utilize a locking feature, such is a metal locking ring or an annular flange.

The acetabular cup assembly may have a two-piece liner that includes a bearing surface component and a capture mechanism. The capture mechanism is locked into the shell after hip reduction.

In another embodiment of the invention, the liner is selected from the group consisting of a constrained liner, a neutral liner, an anteverted liner, a lipped bearing liner, and a lateralized bearing liner.

In yet another embodiment of the invention, the acetabular cup assembly further comprising an installation tool attached to the liner. The installation tool is comprised of metal or plastic.

In one particular embodiment of the invention, the invention is a modular acetabular cup assembly for use with multiple bearing liners. The acetabular cup assembly includes a shell having an inner wall, two annular grooves, and a plurality of anti-rotation tabs. The shell may be used with polyethylene, ceramic, metal, and other types of liners. In the case of a ceramic liner, a band is attached to the liner. The band is adapted to mate with the inner wall. The band on the ceramic liner enables the shell to be used with an off-the-shelf liner without the need for more expensive, custom made liners.

In yet another embodiment of the invention, the shell has a generally concave inner surface, an outer surface, an end face formed at an uppermost end of the shell and an apex formed at a lower end of the shell, a central axis extends through the apex, wherein the inner surface comprises an inwardly-facing scallop defined in the inner surface and extending into the end face. A line extends from where the inner surface meets the lower groove to where the central axis meets a planar surface defined by a plane extending through the face of the shell, the central axis and the line defining an angle, and wherein the angle ranges from about ten degrees to about eighty degrees. In other embodiments, the angle ranges from about forty to about seventy degrees.

In another embodiment of the invention, the first groove and the second groove are separated by a first distance, and the first distance ranges from about one millimeter to about twenty millimeters. In other embodiments, the first distance ranges from about two millimeters to about four millimeters.

In yet another embodiment of the invention, the band has an inner surface and an outer surface spaced apart from the inner surface by a second distance, and the second distance varies from about one-half millimeter to about 30 millimeters. In other embodiments, the distance ranges from about one-half millimeter to about ten millimeters.

The invention offers the advantage of two annular grooves or cavities that receive annular bumps or ribs of the liner.

The grooves may or may not fully extend about an interior of the shell. The use of two ribs and grooves is significant as the effective push-in and push-out of the liner can be controlled and optimized by adjusting the tolerances and dimensions of these four items and the interference between the shell and the liner. Thus, the acetabular cup assembly may be designed such that a surgeon may easily be able to push in the liner by hand but the liner will not disassemble front the shell without the use of a tool.

The band also allows the ceramic liner to be reinserted should this become necessary interoperatively. Furthermore, the band improves the force distribution around the liner and significantly reduces the potential for liner fracture, particularly in the event of a misalignment.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 9 is a partial front perspective view of the acetabular cup assembly shown in

FIG. 8;

FIG. 16 is a front perspective view of the modular acetabular trialing system shown in

FIG. 15;

DETAILED DESCRIPTION OF THE EMBODIMENTS

The following description of the preferred embodiment(s) is merely exemplary in nature and is in no way intended to limit the invention, its application, or uses.

Figure 1:
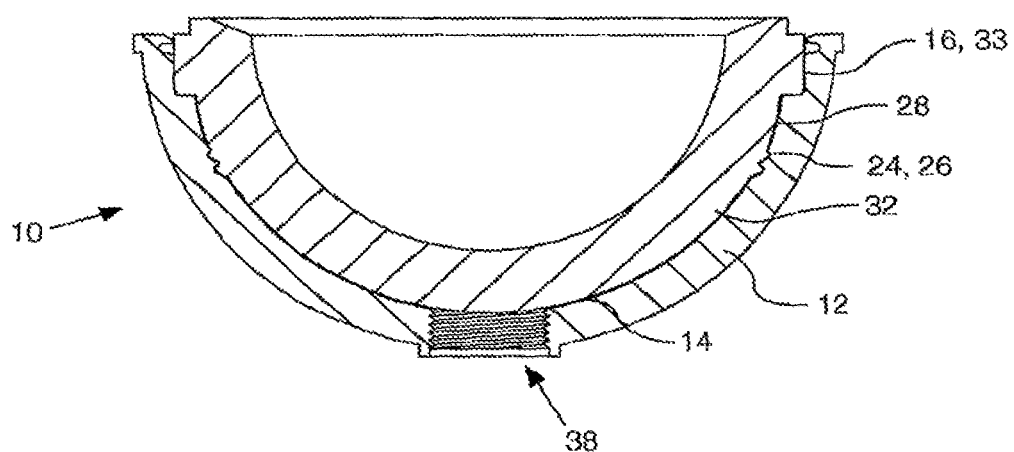
FIG. 1 is a sectional side view of an acetabular cup assembly in a first embodiment.
Figure 2:
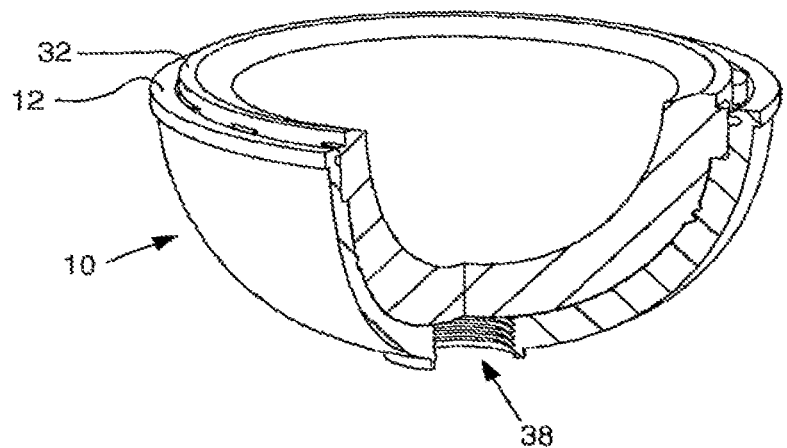
FIG. 2 is a front perspective view of the acetabular cup assembly shown in FIG. 1.

FIGS. 1 and 2 illustrate, an acetabular cup assembly 10. The acetabular cop assembly 10 includes a shell 12. The shell 12 is adapted ferule with multiple bearing linen, such us a first liner 32. The first liner 32 may be any number of liners but is a polymer liner in the embodiment depicted in FIGS. 1 and 2. For example, the first liner 32 may be a cross-linked polyethylene liner or a conventional polyethylene liner. The first liner 32 includes anti-rotation tabs 33. The shell 12 includes an insertion tool hole 38, which is used to receive a tool (not shown) for installation of the shell. In the depicted embodiment, the insertion tool hole 38 is threaded.

Figure 3:
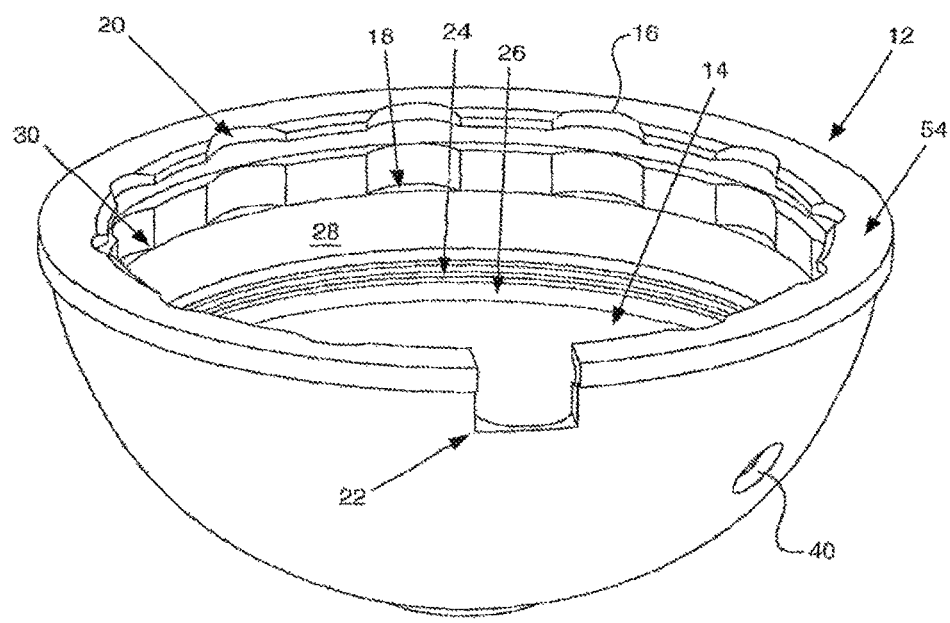
FIG. 3 is a front perspective view of a shell.

As best seen in FIG. 3, the shell 12 includes un inner surface 14. In the embodiment illustrated in FIG. 3, the inner surface 14 has a concave shape but other shapes may be used. In some embodiments, the inner surface 14 is highly polished such that it appears mirror-like. For example, the inner surface may have a roughness from about one microinch to about sixteen microinches. In the depicted embodiment, the inner surface has a roughness from about eight microinches to about sixteen microinches. In some embodiments, the inner surface has a roughness of about 1 microinch to about eight microinches. A highly polished inner surface 14 significantly reduces or prevents polymer liner debris generation.

In the embodiment depicted in FIG. 3, the shell 12 is made of metal but those skilled in the art would understand that other materials could equally be used. As examples, the shell 12 may be made of titanium, cobalt chromium, stainless steel, or other biocompatible material.

The shell 12 includes a face 54 and scallops 16 which receive anti-rotation tabs 33. In the embodiment depicted in FIG. 3, the shell 12 includes twelve scallops 16 and the first liner 33 has twelve corresponding anti-rotation tabs 33 to achieve greater microstability. Each scallop 16 forms a lip or lodge 18 on an inner wall 28 of the shell 12. The shell 12 further includes an annular groove 20 that extends peripherally or circumferentially about the inner wall 28. The shell 12 also includes a notch 22. The notch 22 allows a pry tool access to the liner portion of the assembly.

In some embodiments, the shell 12 may include one or more fixation holes 40. A screw, modular peg, or other fixation device (not shown) may be inserted through the fixation hole 40 to attach the shell 12 to bone. Further, in some embodiments the shell may have a porous coating on its exterior. As examples, the exterior of the shell 12 may have a sintered metal coating, a vapor deposited metal coating, a thermal spray metal coating, or be chemically etched. The porous coating may allow for bone in-growth into the shell 12.

Figure 4A:
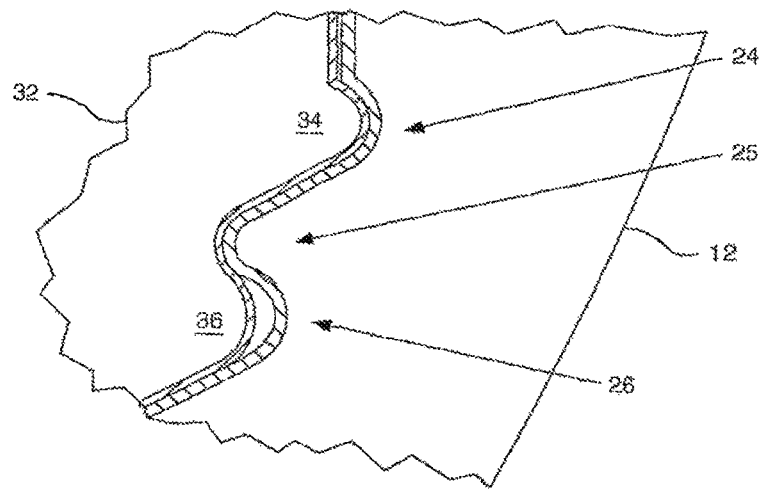
FIG. 4A is a partial sectional side view of the acetabular cup assembly.
Figure 4B:
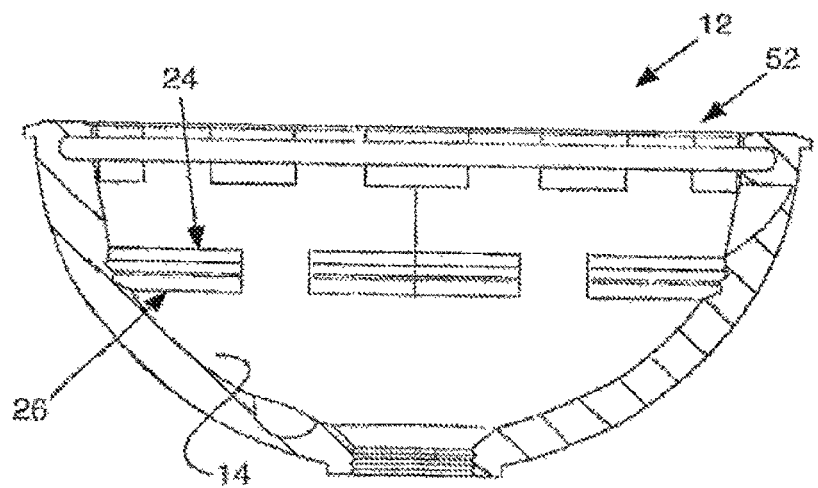
FIG. 4B is a sectional view of an exemplary shell having intermittently spaced grooves.
Figure 4C:
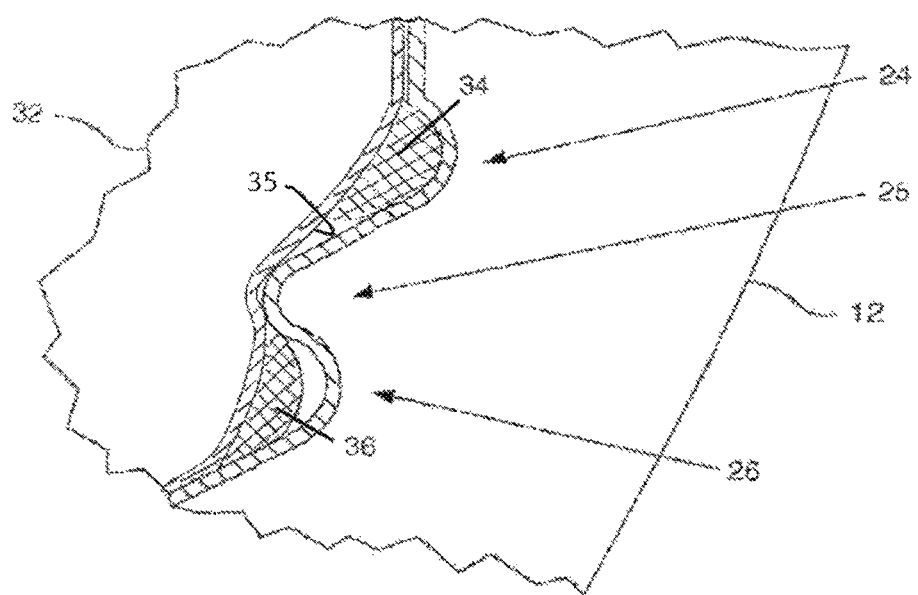
FIG. 4C is a partial sectional view of an exemplary shell having bumps that are separate components coupled to an outer body of the shell and engaged with an adjacent groove.

The shell 12 includes a first groove 24 and a second groove 26. Alternatively, the grooves 24, 26 may be termed indentations or cavities. The grooves 24, 26 may or may not fully extend about an interior 30 of the shell 12. Thus, as seen in FIG. 4B, the groove 24, 26 may form annular rings, have a "C" shape, be intermittently spaced about the circumference, have a hemispherical shape, or have some other shape. As best seen in FIG. 4, the first groove 24 and the second groove 26 respectively receive a first bump 34 and it second bump 36 of the first liner 32. The first bump 34 alternatively may be referred to as a first insertion member or first rib and the second hump 36 alternatively may be referred to as a second insertion member or second rib. As seen in FIG. 4C, in the case of a metal or ceramic liner, the bumps 34, 36 may be a separate component, such as a split ring or spring, or molded to the exterior, or outer body 35, of the liner.

The use of two protrusions and grooves is significant as the effective push-in and push-out of the liner 32 can be controlled by adjusting the tolerances and dimensions of these four items. For example, it is possible to have the liner 32 installed with a small push-in force but also have a significant push-out force. Thus, a surgeon may easily be able to push-in the liner by hand but the liner will not disassemble from the shell without the use of a tool. In another example, the liner 32 may be installed with a high push-in force and have an even greater push-out force. A protrusion 25 is formed in between the grooves 24, 26, and can inwardly extend from an adjacent inner portion of a segment of the inner surface 14. By controlling the interference between she protrusion 25 and the second bump 36 and the other dimensions, one can adjust the push-in and push-out force. If the second bump 36 greatly interferes with the protrusion 25, then the liner 32 will have both a high push-in and push-out. In this case, it may be necessary to significantly cool the liner 32 prior to installation to temporarily reduce its size. However, if the second bump 36 only slightly interferes with the protrusion 25, then the liner 32 may be inserted utilizing a low push-in force and removed utilizing a high push-out force. This is because once the bumps 34, 36 engage the grooves 24, 26, both bumps will contribute to the push out force required. However, in the case of push-in, the force required is only enough for the second bump 36 to clear the protrusion 25 and for the first bump 34 to engage the first groove 24.

The first groove 24 and the second groove 26 are located below the inner wall 28. This is significant because the location of the grooves 24,26 shelters the locking mechanism of the first liner 32 from soft tissue interference. In other words, because the bumps 34, 36 engage the grooves 24, 26 on a lower portion of the shell 12, the likelihood of soft tissue interference with the locking of the first liner 32 to the shell is significantly reduced.

Figure 5:
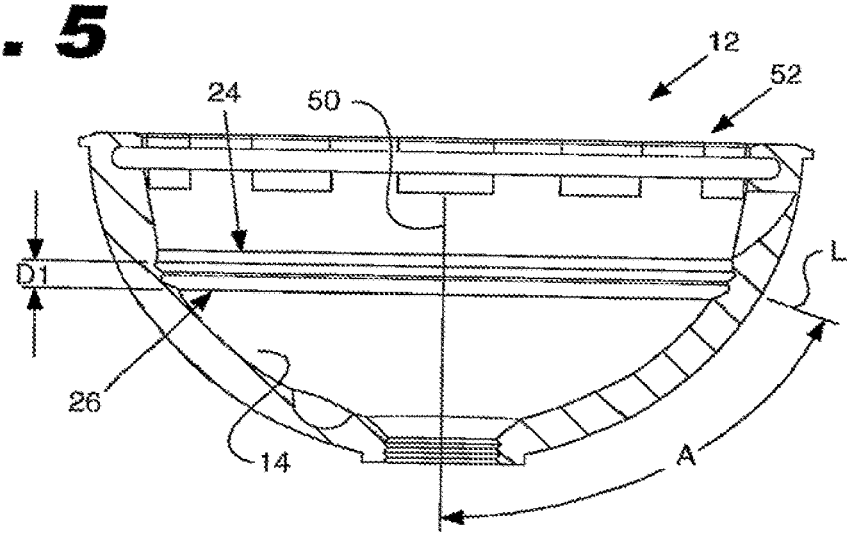
FIG. 5 is a sectional side view of the shell.

FIG. 5 illustrates a view of the shell 12. The shell 12 has a central axis 50 that extends through the apex of the shell. The grooves 24, 26 are located on the inner surface 14 of the shell 12. A line L extends from where the inner surface 14 meets the lower groove 26 to where the central axis 50 meets a planar surface 52. The planar surface 52 is defined by a plane extending through the face 54 of the shell 12. An angle A is defined by the central axis and the line L. The angle A is about 10 degrees to about 80 degrees. In the embodiment depicted in FIG. 5, the angle A is about −40 degrees to about 70 degrees. FIG. 5 also illustrates a first distance or dimension D1. The dimension D1 is the distance between the upper groove 24 and the lower groove 26. The dimension D1 is about 1 to about 20 millimeters. In the embodiment depicted in FIG. 5, the dimension D1 is about 2 to about 4 millimeters.

Figure 6:
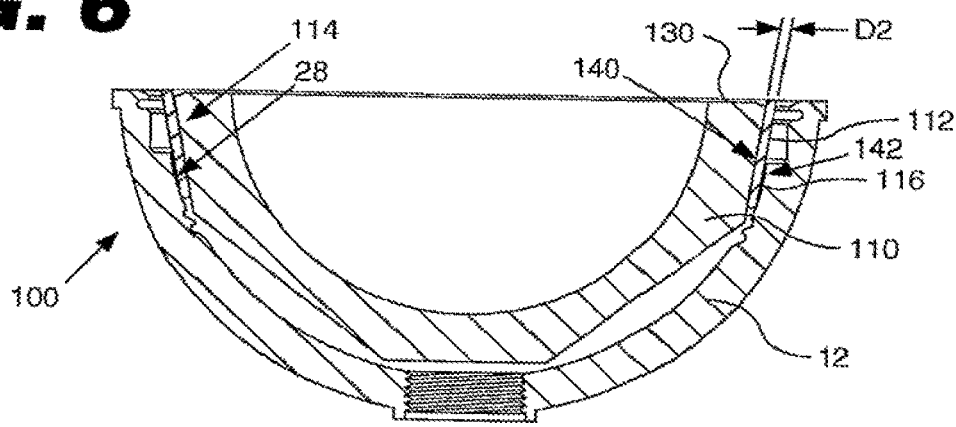
FIG. 6 is a sectional side view of an acetabular cup assembly in a second embodiment.
Figure 7:
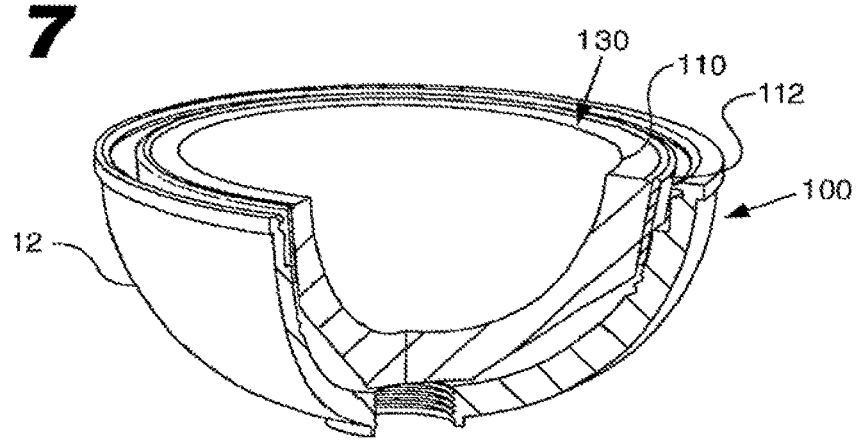
FIG. 7 is a partial from perspective view of Ute acetabular cup assembly shown in FIG. 6.

FIGS. 6 and 7 illustrate a second embodiment of the acetabular cup assembly generally indicated by reference numeral 100. The acetabular cup assembly 100 includes a second liner 110, a band or ring 112, and the shell 12. As an example, the second liner 110 may be a ceramic liner, such as an alumina ceramic liner. Further examples include a diamond liner, a liner made of a polycrystalline diamond composite material, a liner made from oxidized zirconium, or a liner made from polyethylene, including cross linked polyethylene. The band 112 may be made of metal. For example, the band 112 may be made of stainless steel, titanium, cobalt chromium, or a shape memory alloy, such as nitinol. The band 112 is affixed to an outer portion 114 of the liner 110. The band 112 is adapted to mate with the inner wall 28 of the shell 12. The band 112 and the inner wall 28 may be tapered. For example, the inner wall 28 may be tapered from about two degrees to about thirty-six degrees. In the embodiment depicted in FIG. 6, the inner wall 28 has about an eighteen degree taper. The band 112 allows a ceramic liner to be removed and reinserted. This is significant, as previously removal and reinstallation of a ceramic liner was inadvisable. Further, the band 112 improves the force distribution around the second liner 110 and eliminates, or at least significantly reduces, the potential for cracking of a ceramic liner upon insertion, especially if there is any misalignment. The liner 110 has a face 130. The band 112 may extend above the face 130, below the face 130, or substantially flush with the face 130. If the band 112 extends above the face 130, the band 112 may prevent impingement in some circumstances. In the embodiment depicted in FIGS. 6 and 7, the band is substantially flush with the lace 130.

The band 112 has an inner surface 140 and an outer surface 142 spaced apart from the inner surface 140. The inner surface 140 is sized and shaped to compliment the outer portion 114 of the liner 110, and the outer surface 142 is sized and shaped to compliment the inner wall 28. The outer surface 142 is spaced apart from the inner surface 140 by a second distance or second dimension D2. The distance D2 may vary from about one-half millimeter to about 30 millimeters, and rather from about one-half millimeter to about ten millimeters. In the embodiment depicted in FIG. 6, the distance D2 is about three-fourths of a millimeter.

In some embodiments, the shell 12 way accept differently sized liners. The acetabular cup assembly 100 may include a plurality of liners, each having a band with a differently sized inner surface but each having the same size outer surface. Thus, the plurality of liners all fit the same shell because the outer surface is the same size. However, the inner surface is differently sized allowing for differently sized liners, the difference in size is adjusted by adjusting the distance D2 of the band 112. As an example only, the single shell 12 may accept 26, 28, and 32 millimeter inner diameter liners. This is significant as the modularity reduces manufacturing costs and provides surgeons with a greater number of interoperative choices.

In outer embodiments, the liner 110 may fit within differently sized shells. The acetabular cup assembly 100 may include a plurality of liners, each having a band with a differently sized outer surface hut each having the same size inner surface. Thus, the plurality of liners each have the same inner diameter size but has differently sized outer surface that compliments a particular size of shell. The difference in size is adjusted by adjusting the distance D2 of the band 112. As an example only, the single liner 110 may fit within 46, 48, and 50 millimeter inner diameter shells. This is significant as the modularity within manufacturing costs and provides surgeons with a greater number of intraoperative choices.

Figure 8:
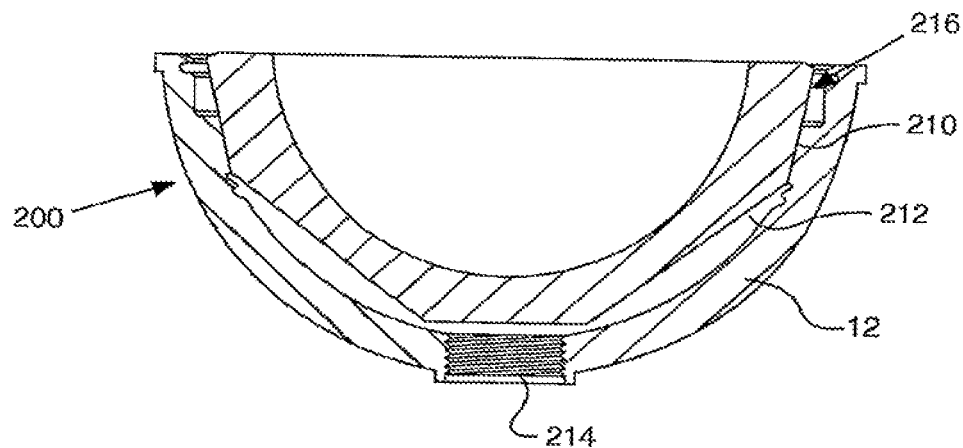
FIG. 8 is a sectional side view of an acetabular cup assembly in a third embodiment.
Figure 9:
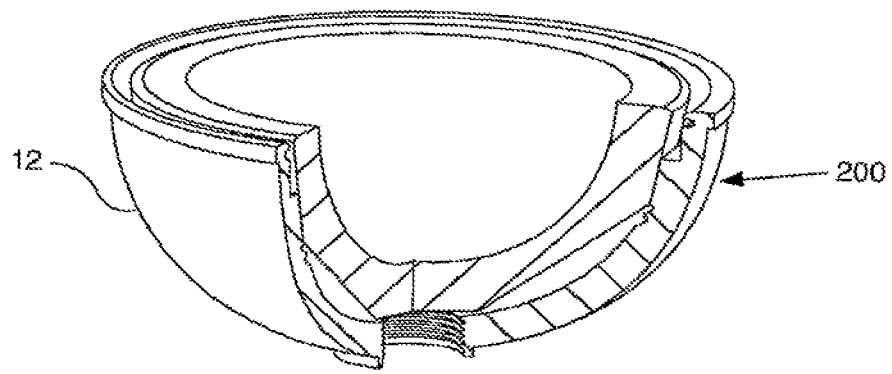

FIGS. 8 and 9 illustrate a third embodiment of the acetabular cup assembly, generally indicated by reference numeral 200. The acetabular cup assembly 200 includes a third liner 212 and the shell 12. As an example, the third liner 212 may be a metal liner, such as cobalt chromium. Alternatively, the third liner 212 may be a ceramic, plastic, or composite. The liner 212 includes an outer portion 216. The outer portion 216 is adapted to mate with the inner wall 28 of the shell 12. The outer portion 216 and the inner wall 28 may be tapered. For example, the inner wall 28 may be tapered from about two degrees to about thirty-six degrees. In the embodiment depicted in FIG. 8, The inner wall 28 has about an eighteen degree taper. In some embodiments, the assembly 200 may further include plug 214. The plug 214 may be used to cover fixation devices or used to fill unused holes. In FIG. 9, the plug 214 has been removed for clarity.

Figure 10:
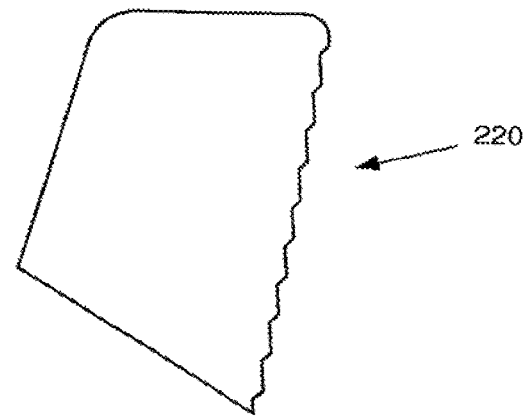
FIG. 10 is a first embodiment of a surface enhancement.
Figure 11:
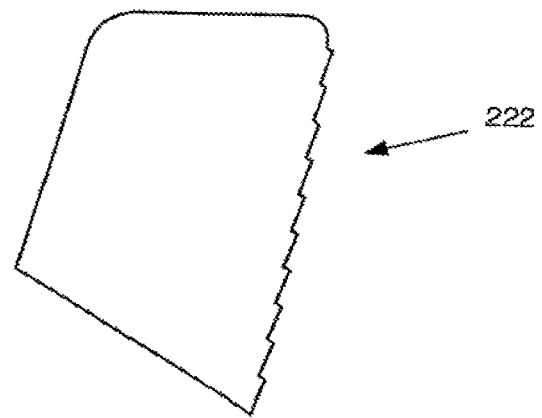
FIG. 11 is a second embodiment of a surface enhancement.
Figure 12:
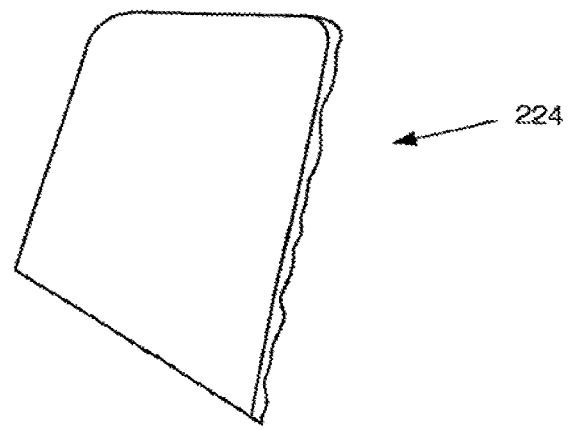
FIG. 12 is a third embodiment of a surface enhancement.

FIGS. 10, 11, and 12 illustrate various surface enhancements that may be applied to the band 112 or the outer portion 214 for lock enhancement of the liner. In FIG. 10, an Acme-type "stair-step" 220 may be machined into the band 112 or the outer portion 216. Similarly, in FIG. 11 a "reverse stair-step" 222 may be machined into the band 112 or the outer portion 216. The stair-step surface configuration 220 or are reverse stair-step configuration may be lined to maintain lock integrity even after multiple reinsertions. In FIG. 12, the band 112 or the outer portion 216 may have predetermined surface roughness 224. The surface roughness 224 may be achieved by coarse media blasting, such as by grit blast, glass bead blast etc. Alternatively, the surface enhancements 220, 222, 224 could be applied to the inner wall 28. Moreover, numerous types of coatings may be applied to the band 112, the outer portion 214, or the inner wall 28. As examples, these surfaces may have a metal, plastic, diamond, or composite coating.

Figure 13:
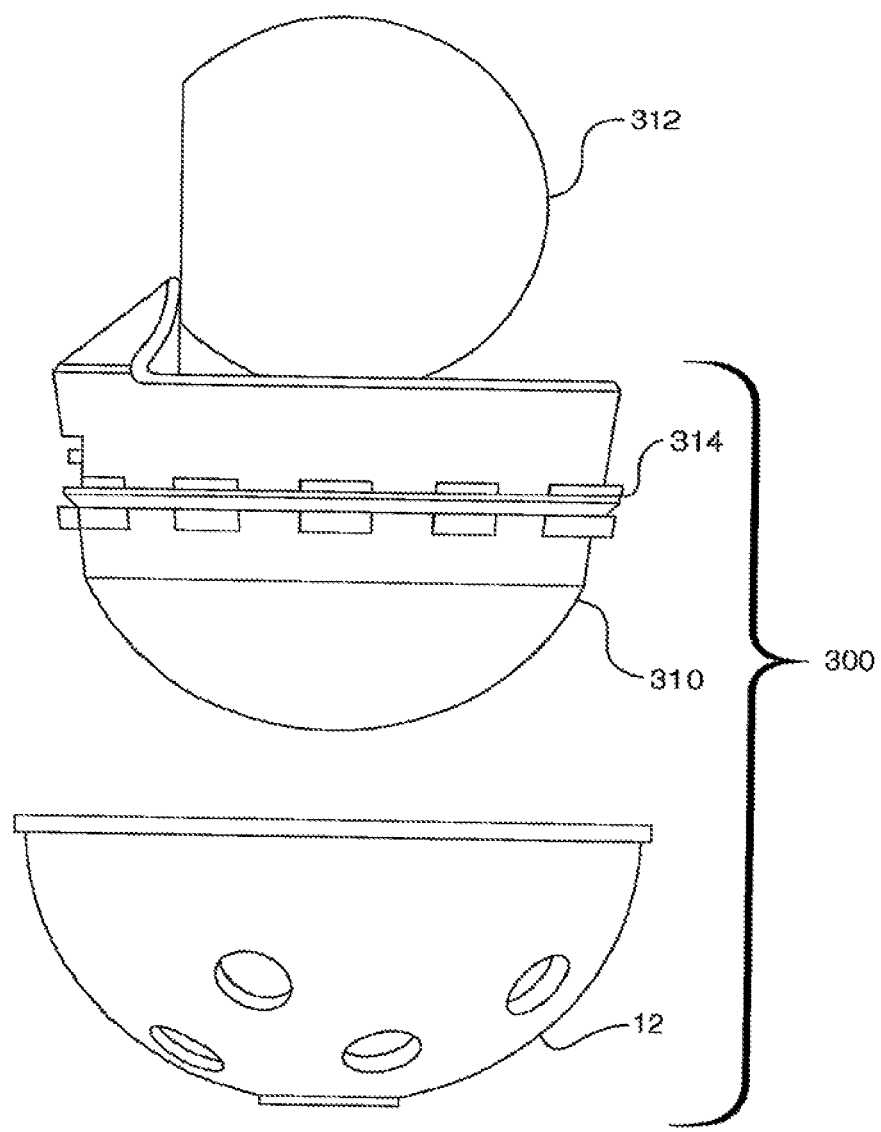
FIG. 13 is an exploded side view of an acetabular cup assembly in a fourth embodiment.

FIG. 13 illustrates a fourth embodiment of the acetabular cup assembly, generally indicated by reference numeral 300. The acetabular cup assembly 300 includes the shell 12 and a constrained bearing liner 310. In a constrained bearing liner, a femoral head 312 is captured within the liner. Constrained bearing liners often utilize a third locking feature as they typically require a higher disassociation force. In FIG. 13, a metal locking ring 314 interfaces with the first groove 24. Alternatively, an annular flange may be attached to the liner and the annular flange engages the first groove 24. The locking ring 314 may be used with either a one-piece or two-piece constrained liner construct.

Figure 14:
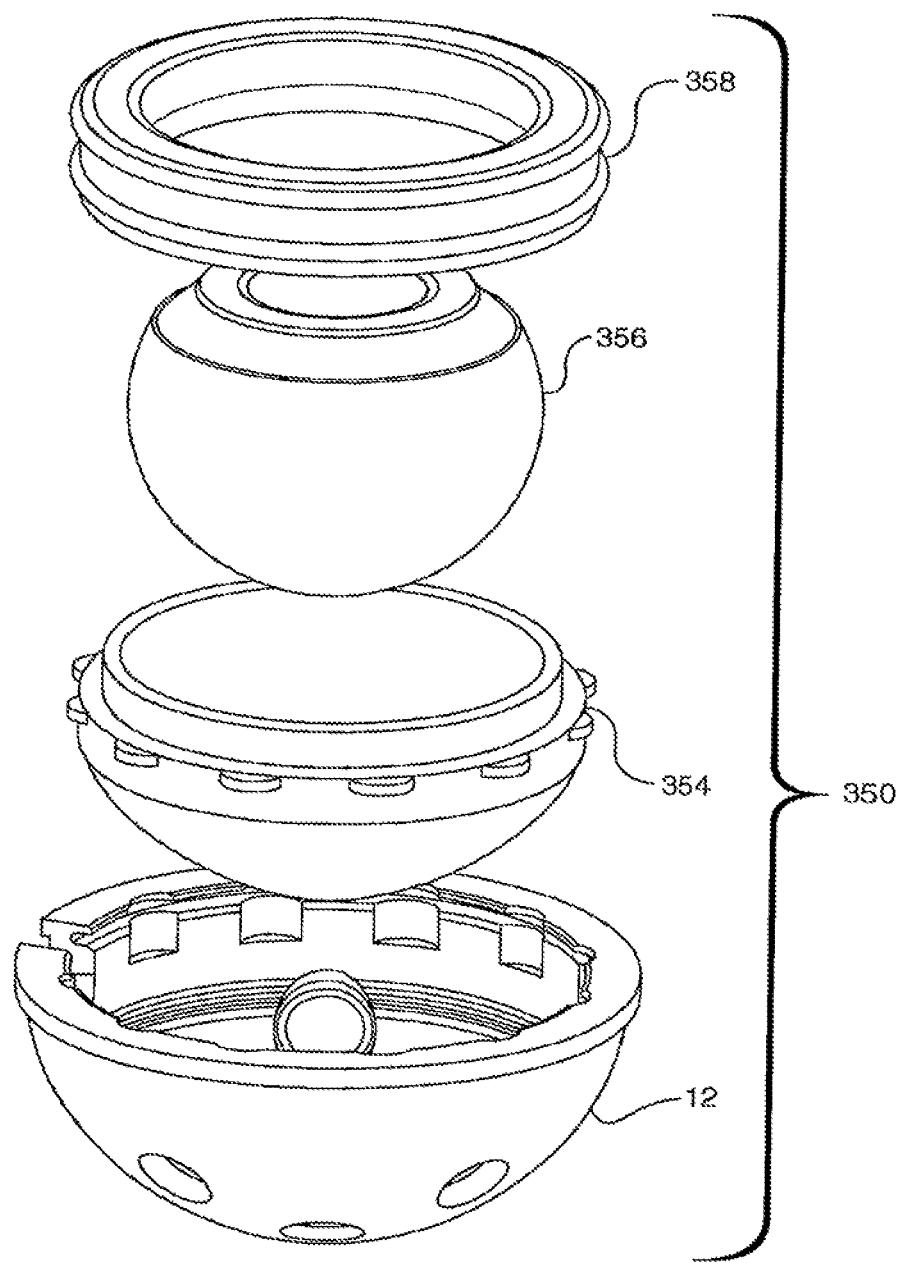
FIG. 14 is an exploded side view of in acetabular cup assembly in a fifth embodiment.

FIG. 14 illustrates a fourth embodiment of the acetabular cup assembly, generally indicated by reference numeral 350. The acetabular cup assembly is a two-piece construct that includes the shell 12, a bearing surface component 354, and a capture mechanism 358. For the two-piece construct, the bearing surface component 354 is inserted into the shell, the femoral head 356 is placed in the liner, and the capture mechanism 358 is placed over the femoral component 356 prior to head assembly. Once the hip is reduced, the capture mechanism 358 is inserted and locked into the shell thereby securing the full assembly construct. As an example, the capture mechanism may engage the annular groove 20 (best teen in FIG. 3).

The liners 32, 110, 212, 310, 354 may be neutral liners, anteveretd bearing liners, lipped bearing liners, or lateralized bearing liners. Thus, the depicted embodiments are merely exemplary. Further, an interior or an exterior of the linen 32, 110, 212, 310, 354 may be coated with various types of coatings. For example, these surfaces may have a metal, plastic, diamond, or composite coating.

Figure 15:
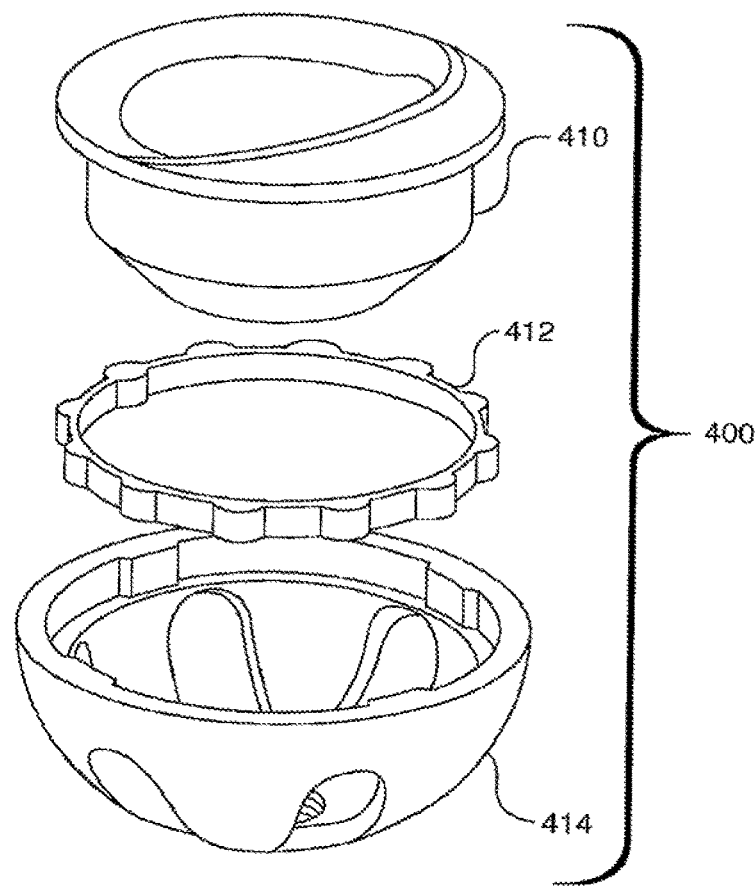
FIG. 15 is an exploded front perspective view of a modular acetabular trialing system.
Figure 16:
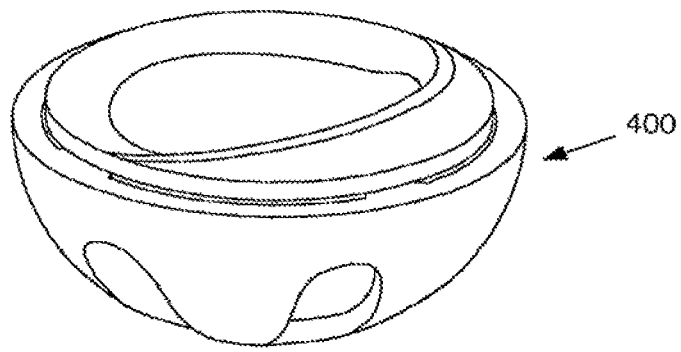
Figure 17:
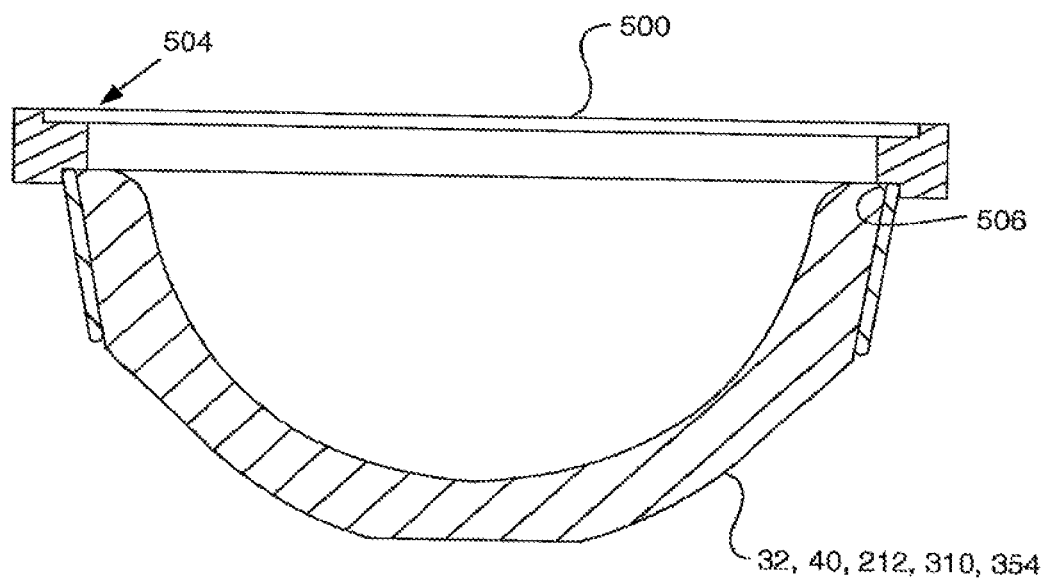
FIG. 17 is a sectional side view of an installation tool in a first embodiment in use on a liner.
Figure 18:
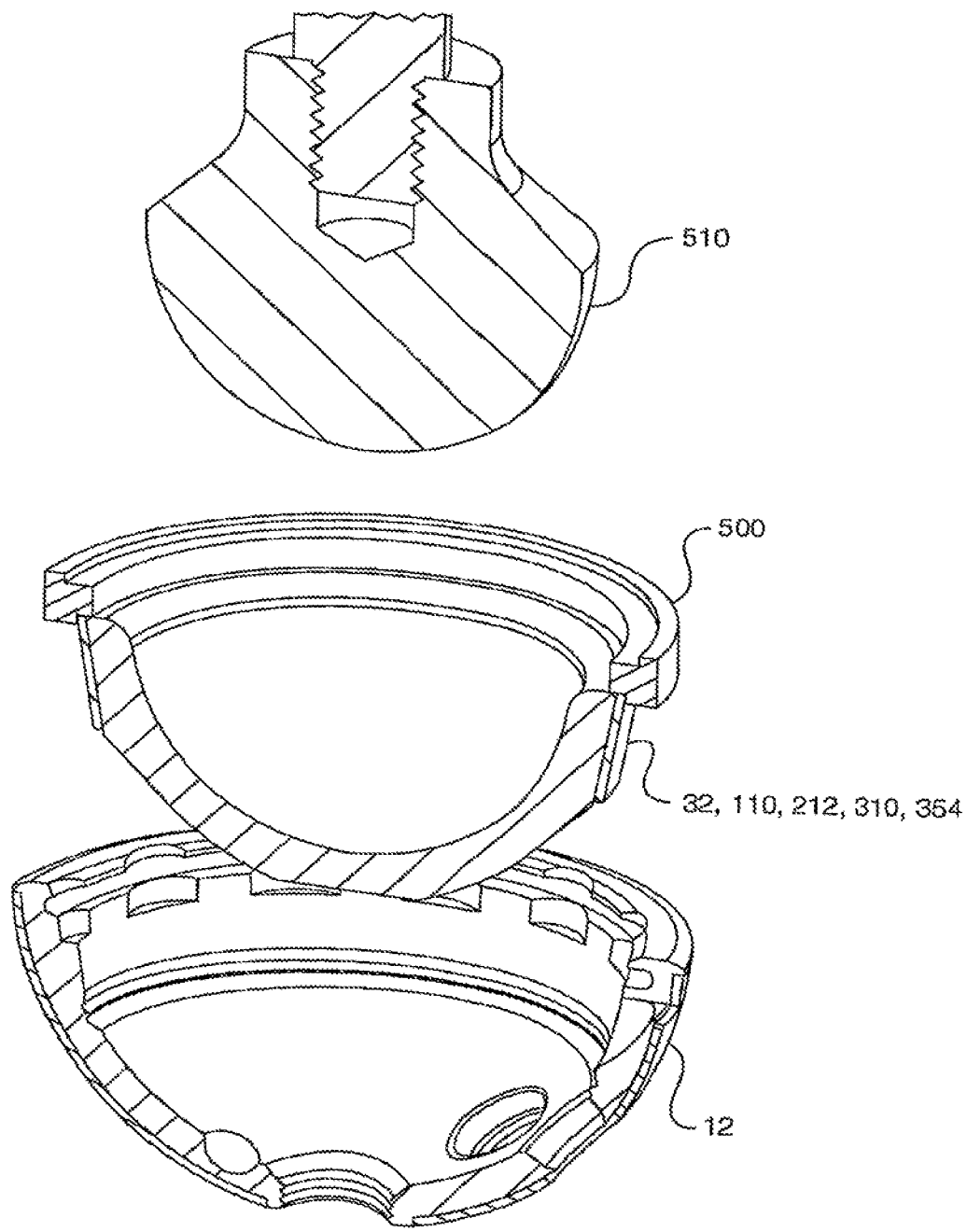
FIG. 18 is a front perspective exploded sectional view of the shell, the installation tool applied to the liner, and an impactor head.
Figure 19:
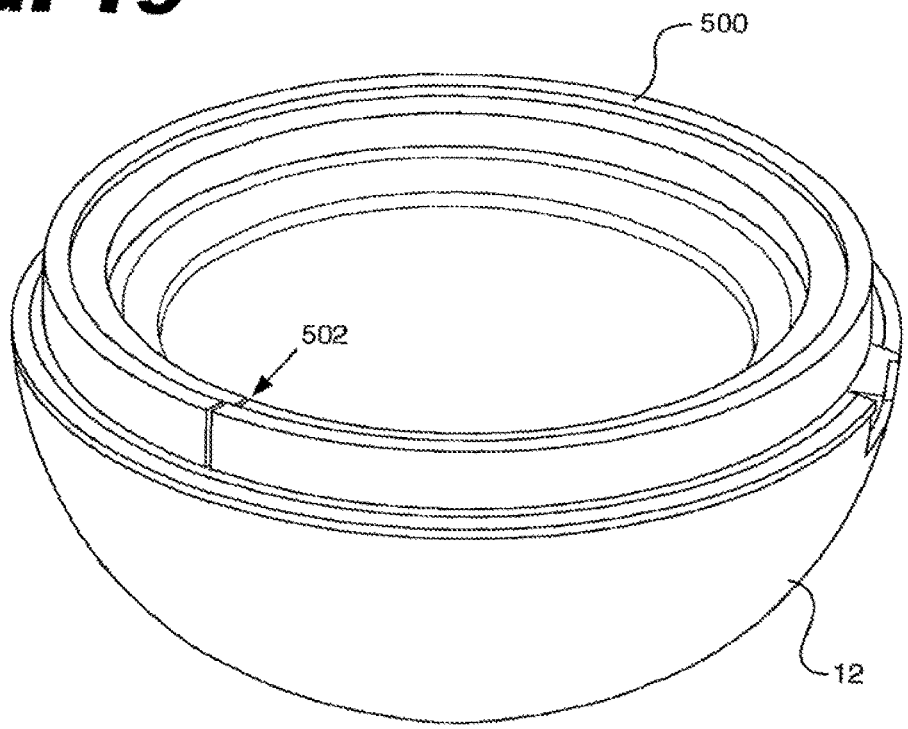
FIG. 19 is a front perspective view of the shell, installation tool, and liner.
Figure 20:
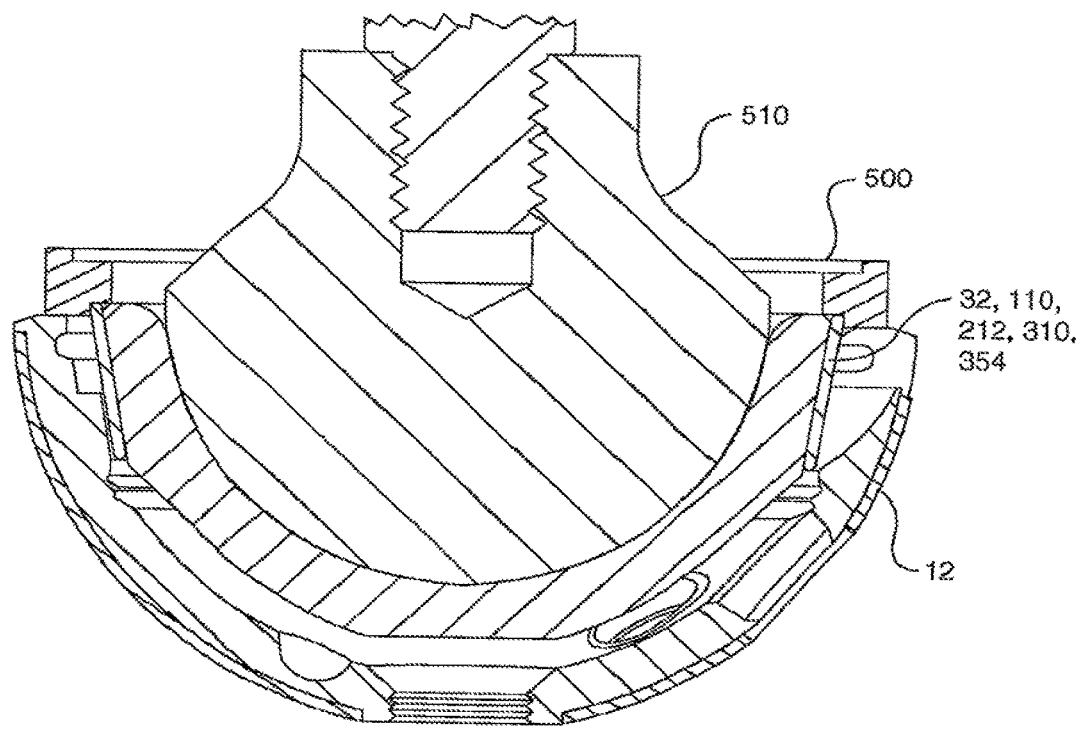
FIG. 20 is a sectional side view of the shell, the installation tool applied to the liner, and the impactor head.

FIGS. 15 and 16 illustrate a modular acetabular trialing system 400. The acetabular trialing system 400 includes a trial liner 410, a trial spacer 412, and a trial shell 414. Modularity greatly reduces the number of trialing components necessary to cover the full range of sizes offered in the acetabular cup system, which further simplifies the amount of instrumentation required for surgery. The trial liner 410 and the trial spacer 412 may be used with the trial shell 414 or the implantable shell 12.

FIGS. 17, 18, 19 and 20 illustrate a method and apparatus for installing the liner 32, 110, 212, 310, 354. A first embodiment of an installation tool 500 is attached to the liner 32, 110, 212, 310, 354. The installation tool 500 is substantially circular. In some embodiments, the installation tool 500 has a cutout 502. The installation tool 500 has a first shoulder 504 and a second shoulder 506. Alternatively, these features may be termed as a first capture, recess 504 and a second capture recess 506. In some embodiments, the first shoulder is identical to the second shoulder such that either side of the installation tool may be used. In outer embodiments, the first shoulder 504 is larger or smaller than the second shoulder 506 such that the installation tool 500 may accommodate various sizes of liners 32, 110, 212, 310, 354. The first shoulder 504 and the second shoulder 506 may be square or tapered. In the tapered embodiments, the first and second shoulders 504, 506 may taper outwardly for manufacturing purposes or taper inwardly to provide line contact with the liner.

In the method, the installation tool 500 is slightly spread open and attached to the liner 32, 110, 212, 310, 354 until either the first shoulder 504 or the second shoulder 506 contact the liner. The installation tool 500 is resilient and biased to spring back into its original position. Thus, the installation tool 500 is attached to the liner 32, 110, 212, 310, 354 through the use of a spring force.

Once the installation tool 500 is assembled to the liner 32, 110, 212, 310, 354, the installation tool 500 and the liner 32, 110, 212, 310, 354 are placed over the shell 12. Thereafter, an impactor head 510 may be used to press on the liner 32, 110, 212, 310, 354 to remove the liner from the installation tool 500 and install the liner in the shell 12. The use of the installation tool 500 allows for automatic centering and alignment of the liner 32, 110, 212, 310, 354 within the shell 12. The use of the installation tool 500 significantly reduces the possibility that the liner may become askew relative to the shell upon installation. Further, the installation tool 500 may serve as a soft tissue retractor during installation. The outer portion of the installation tool 500 may be used to push soft tissue aside as the liner is inserted into the shell.

The installation tool 500 may be re-usable or disposable. For example, the installation tool 500 may be made of metal, such as stainless steel, and the installation tool may be sterilized and re-used after installation of the liner. Alternatively, the installation tool 500 may be made from a polymer or plastic and disposed of after liner insertion. In the case of a plastic material, the installation tool may be color coded to indicate a particular size or to indicate a particular brand.

Figure 21:
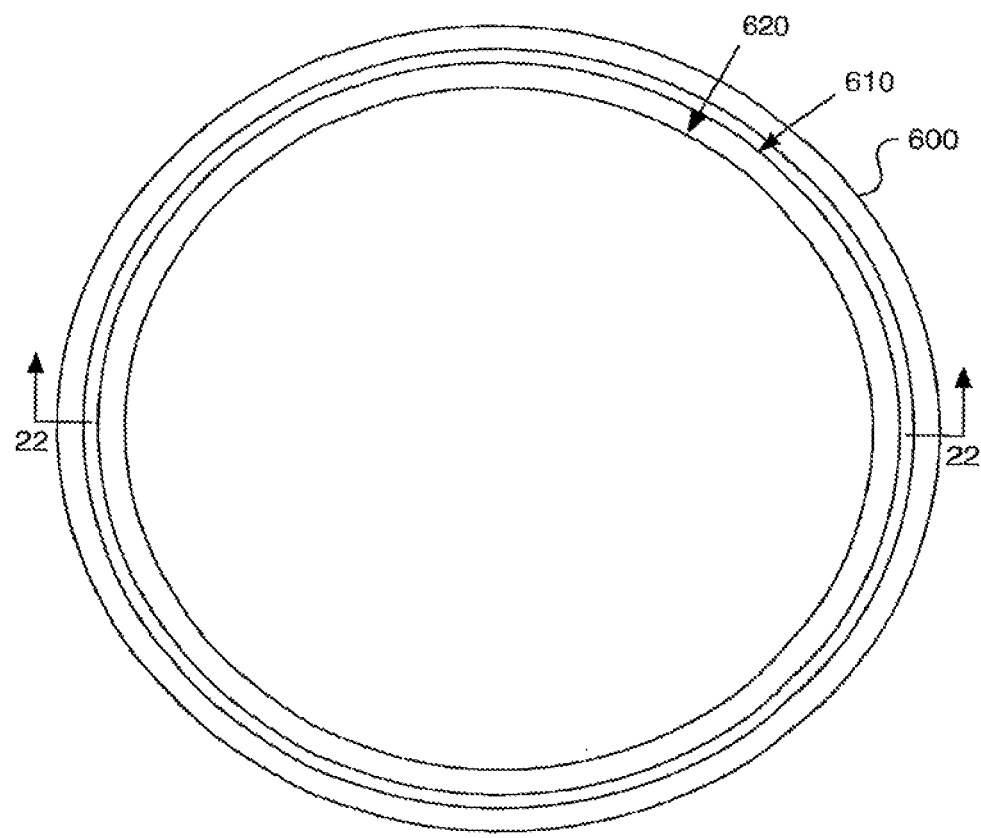
FIG. 21 is a top view of the installation tool in a second embodiment.
Figure 22:
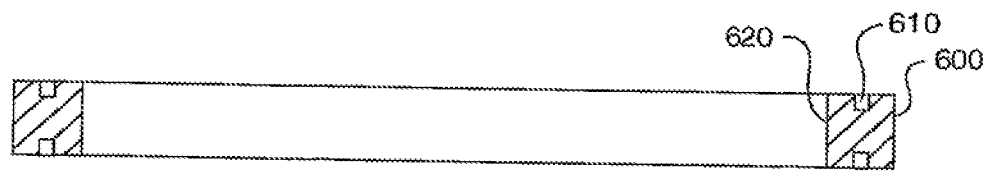
FIG. 22 is a sectional front view of the embodiment shown in FIG. 21.

FIGS. 21 and 22 illustrate a second embodiment of the installation tool, generally indicated by numeral reference 600. The installation tool 600 includes a notch 610. The notch 610 allows an inner portion 620 of the installation tool 600 to flex. Thus, the bending of the inner portion 620 provides a spring force that can be applied in the liner 32, 110, 212, 310, 354. Similar to the first embodiment, the installation tool 600 is assembled to the liner 32, 110, 212, 310, 354, the installation tool 600 and the liner are placed over the shell 12. Thereafter, an impactor head 510 may be used to press on the liner to remove the liner from the installation tool 600 and install the liner in the shell 12. The use of the installation tool 600 allows for automatic centering and alignment of the liner within the shell 12.

Figure 23:
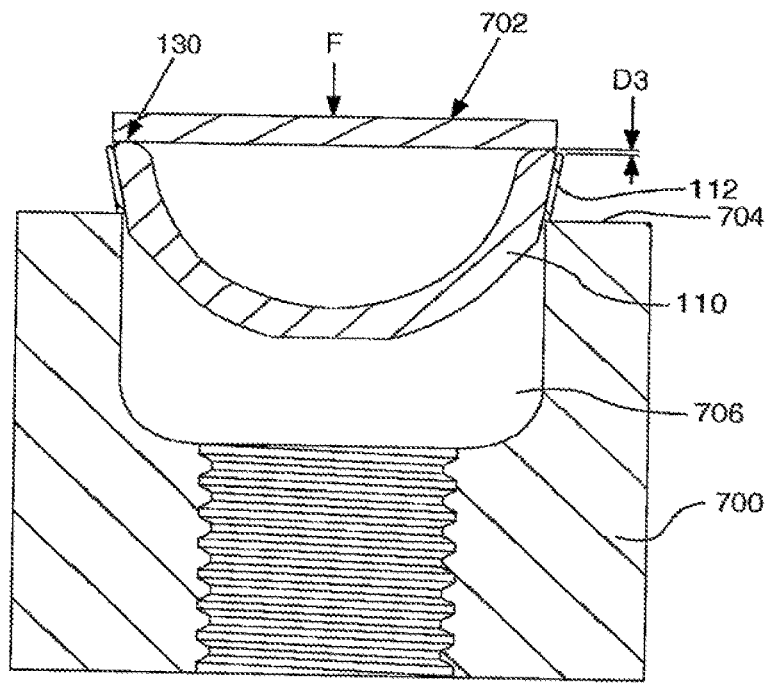
FIG. 23 is a sectional front view of a fixture for mounting a band to a liner in a first embodiment.

FIG. 23 illustrates a first embodiment of a fixture 700 for use in installing the band 112 on the liner 110. The fixture 700 includes a fixture face 704 and a well 706. To install the band 112 on the liner 110, the band 112 and the liner 110 are placed on the fixture 700 and a press (not shown) with a press platen 702 is used to press the band 112 on the liner 110. First, the fixture 700 is mounted to the press, which may be a computer numerically controlled press. Second, the press is set with a displacement rate, a minimum force, and a maximum force. The displacement rate may be from about 0.01 inch per minute to about 2.00 inches per minute maximum. In the depicted embodiment, the displacement rate is about 0.80 inches per minute to about 1.10 inches per minute maximum. The minimum force ranges from about 5000 pounds to 11000 pounds. In the depicted embodiment, the minimum force is about 8000 pounds. The maximum force ranges from about 8000 pounds to about 15000 pounds. In the depicted embodiment, the maximum force is about 10000 pounds. Third, the band 112 is placed on the liner 110 by hand. Fourth, the band 112 and the liner 110 are placed on the fixture 700 with the liner 110 protruding into the well 706 and the hand 112 resting on the fixture face 704. Fifth, the press platen 702 is advanced until it makes contact with me face 130 of the liner 110. The initial preload force on the liner 110 may be from about zero pounds to about ten pounds. Sixth, the press platen 702 applies a force F on the liner 110 until a displacement D3 is achieved between the band 112 and the liner 110. The displacement D3 is zero with a tolerance of one millimeter in either direction. Optimally, the displacement D3 is zero with a tolerance of about one-quarter of a millimeter in either direction. Thereafter, the assembled hand 112 and the liner 110 are inspected for material transfer blemishes. A microscope may be used to inspect the assembly.

Figure 24:
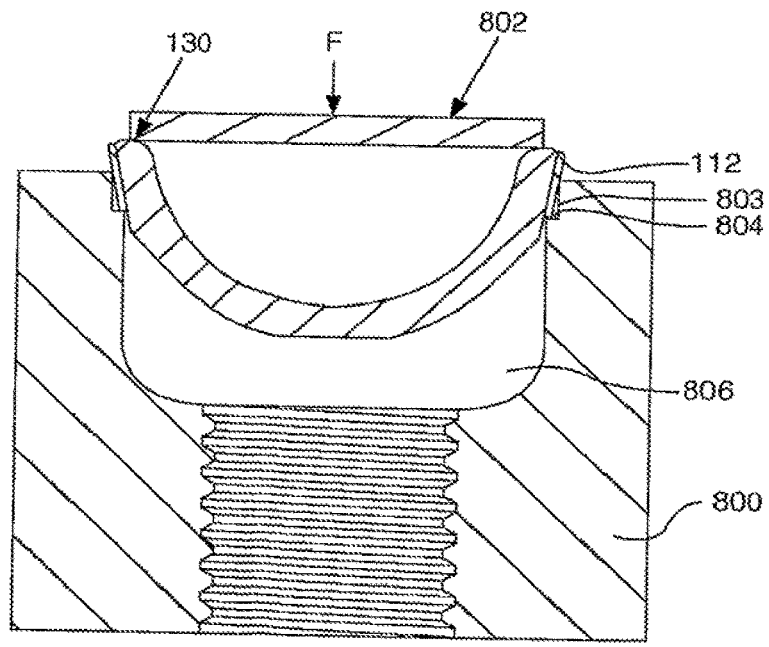
FIG. 24 is a sectional front view of a fixture for mounting a band to a liner in a second embodiment.

FIG. 24 illustrates a second embodiment of a fixture 800 for use in installing the band 112 on the liner 110. The fixture 800 includes a counter bore 803, a fixture face 804 and a well 806. To install the band 112 on the liner 110, the band 112 and the liner 110 are placed on the fixture 800 and a press (not shown) with a press platen 802 is used to press the band 112 on the liner 110. First, the fixture 800 is mounted to the press, which may be a computer numerically controlled press. Second, the press is set with a displacement rate, a minimum force, and a maximum force. The displacement rate may be from about 0.01 inch per minute to about 2.00 inches per minute maximum. In the depicted embodiment, the displacement rate is about 0.80 inches per minute to about 1.10 inches per minute maximum. Thu minimum force ranges from about 5000 pounds to 11000 pounds. In the depicted embodiment, the minimum force is about 8000 pounds. The maximum force ranges from about 8000 pounds to about 15000 pounds. In the depicted embodiment, the maximum force is about 10000 pounds. Third, the band 112 is placed on the liner 110 by hand. Fourth, the band 112 and the liner 110 are placed on the fixture 800 with the liner 110 protruding into the well 806 and the band 112 resting in the counter bore 803 and on the fixture face 804. The counter bore 803 provide the advantage of self-centering the assembly over the well 806. Fifth, the preys platen 802 is advanced until it makes contact with the face 130 of the liner 110. The initial preload force on the liner 110 may be from about zero pounds to about ten pounds. Sixth, the press platen 802 applies a force F on the liner 110 until a displacement D3 is achieved between the hand 112 mid the liner 110. The displacement D3 is zero with a tolerance of one millimeter in either direction. Optimally, the displacement D3 is zero with a tolerance of about one-quarter of a millimeter in either direction. Thereafter, the assembled hand 112 and the liner 110 are inspected for material transfer blemishes. A microscope may be used to inspect the assembly.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while the first groove and the second groove have been depicted as annular, those of ordinary skill in the art would understand that the grooves may be intermittently spaced about the inner surface of the shell and still achieve the same function. Thus, the breadth and scope of the present invention should not be limited by any of the above-described exemplary embodiments, but should be defined only in accordance with the following claims appended hereto and their equivalents.

The invention claimed is:

1. An acetabular cup system, comprising:
a shell having a generally concave inner surface, an outer surface, an end face formed at an uppermost end of the shell, an apex formed at a lower end of the shell, and a central axis extending through the apex, wherein the inner surface comprises an inwardly-facing scallop defined in the inner surface and extending into the end face, at least a portion of the inner surface defining a taper with respect to the central axis, the tapered portion of the inner surface extending below the scallop, a protrusion located below the tapered portion of the inner surface, and a lower groove located below the protrusion;
a first liner comprising generally convex first outer portion, the first outer portion including an outwardly-extending tab and a lower bump, wherein the first liner is formed of a polymer material; and
a second liner comprising a generally convex second outer portion, the second outer portion including a tapered outer wall, wherein the second liner is formed of a metallic material;
wherein the shell is configured to receive each of the first liner and the second liner;
wherein when the first liner is seated in the shell, the tab is received in the scallop, the lower bump is received in the lower groove and engaged with a lower side of the protrusion, and an interference fit is formed between the first liner and the shell, the interference fit including at least engagement of the lower bump with the lower groove; and wherein when the second liner is seated in the shell, the tapered outer wall is engaged with the tapered portion of the inner surface upper wall of the shell, and the second liner is retained in the shell by engagement between the tapered portion of the inner surface and the upper wall.

2. The system of claim 1, further comprising a third liner including a generally convex third outer portion, the third outer portion including a second tapered outer wall; wherein the third liner is formed of a ceramic material; and wherein when the third liner is seated in the shell, the tapered portion of the inner surface is engaged with the second tapered outer wall, and the third liner is retained in the shell by engagement of the tapered portion of the inner surface with the second tapered outer wall.

3. The system of claim 2, further comprising a tapered band; wherein when the third liner is seated in the shell, the tapered band is positioned between the tapered portion of the inner surface and the second tapered outer wall such that the tapered portion of the inner surface is engaged with the second tapered outer wall through the tapered band.

4. The system of claim 1, wherein a portion of the wall extending below the tapered portion defines an upper groove, and wherein the first liner further comprises an upper bump sized and shaped to be received in the upper groove.

5. The system of claim 4, wherein a distance between the upper groove and the lower groove is between two millimeters and four millimeters.

6. The system of claim 1, wherein the lower groove has a curved cross-section along a plane including the central axis.

7. The system of claim 4, wherein the protrusion is positioned between the lower and upper grooves.

8. The system of claim 1, wherein the lower groove is partially defined by the protrusion.

9. The system of claim 1, wherein the inwardly-facing scallop includes a plurality of scallops and the outwardly-extending tab of the first liner includes a plurality of tabs sized and shaped to be received in the plurality of scallops.

10. The system of claim 1, wherein, the inner surface of the shell has a polished finish, and the tapered outer wall of the second liner has a roughened finish.

11. The system of claim 10, wherein a surface roughness of the inner surface is less than 16 microinches.

12. An acetabular cup system, comprising:
a shell having a generally concave inner surface, an outer surface, an end face formed at an uppermost end of the shell, an apex formed at a lower end of the shell, and a central axis extending through the apex, wherein the inner surface comprises an inwardly-facing scallop defined in the inner surface and extending into the end face, at least a portion of the inner surface defining a taper with respect to the central axis, the tapered portion of the inner surface extending below the scallop, a protrusion located below the tapered portion of the inner surface, a lower groove located below the protrusion, and an upper groove formed in a portion of the wall extending below the tapered portion;
a first liner comprising generally convex first outer portion, the first outer portion including an outwardly-extending tab, an upper bump, and a lower bump, wherein the first liner is formed of a polymer material; and a second liner comprising a generally convex second outer portion, the second outer portion including a tapered outer wall, wherein the second liner is formed of a metallic material;

wherein the shell is configured to receive each of the first liner and the second liner;

wherein when the first liner is seated in the shell, the tab is received in the scallop, the upper bump is received in the upper groove, the lower bump is received in the lower groove and engaged with a lower side of the protrusion, and an interference fit is formed between the first liner and the shell, the interference fit including at least engagement of the upper bump with the upper groove and the lower bump with the lower groove; and wherein when the second liner is seated in the shell, the tapered outer wall is engaged with the tapered portion of the inner surface upper wall of the shell, and the second liner is retained in the shell by engagement between the tapered portion of the inner surface and the upper wall.

13. The system of claim 12, further comprising a third liner including a generally convex third outer portion, the third outer portion including a second tapered outer wall; wherein the third liner is formed of a ceramic material; and wherein when the third liner is seated in the shell, the tapered portion of the inner surface is engaged with the second tapered outer wall, and the third liner is retained in the shell by engagement of the tapered portion of the inner surface with the second tapered outer wall.

14. The system of claim 12, wherein a distance between the upper groove and the lower groove is between two millimeters and four millimeters.

15. The system of claim 12, wherein the protrusion is positioned between the lower and upper grooves.

16. The system of claim 12, wherein the inwardly-facing scallop includes a plurality of scallops and the outwardly-extending tab of the first liner includes a plurality of tabs sized and shaped to be received in the plurality of scallops.

* * * * *